United States Patent
Souza et al.

(10) Patent No.: US 10,487,059 B2
(45) Date of Patent: Nov. 26, 2019

(54) CRYSTALLINE FORM OF ELUXADOLINE

(71) Applicant: Apotex Inc., Toronto (CA)

(72) Inventors: Fabio E. S. Souza, Mississauga (CA); Bahareh Khalili, Mississauga (CA); Annyt Bhattacharyya, Hamilton (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/139,352

(22) Filed: Sep. 24, 2018

(65) Prior Publication Data

US 2019/0092734 A1  Mar. 28, 2019

Related U.S. Application Data

(60) Provisional application No. 62/562,654, filed on Sep. 25, 2017.

(51) Int. Cl.
*C07D 233/64* (2006.01)
*A61P 1/12* (2006.01)
*A61K 9/20* (2006.01)

(52) U.S. Cl.
CPC .............. *C07D 233/64* (2013.01); *A61K 9/20* (2013.01); *A61P 1/12* (2018.01); *C07B 2200/13* (2013.01)

(58) Field of Classification Search
CPC .......................... A61K 31/625; C07D 233/64
See application file for complete search history.

(56) References Cited

U.S. PATENT DOCUMENTS

| | | | |
|---|---|---|---|
| 7,041,681 B2 | 5/2006 | Breslin et al. | |
| 7,994,206 B2 | 8/2011 | Anzalone et al. | |
| 2016/0015724 A1* | 1/2016 | Anzalone | A61K 31/625 548/338.1 |
| 2018/0228773 A1 | 8/2018 | Marinkovic et al. | |

FOREIGN PATENT DOCUMENTS

| | | |
|---|---|---|
| WO | 03092688 A2 | 11/2003 |
| WO | 2009009480 A2 | 1/2009 |
| WO | 2017015606 A1 | 1/2017 |
| WO | 2017114446 A1 | 7/2017 |
| WO | 2017153471 A1 | 9/2017 |
| WO | 2018046028 A1 | 3/2018 |
| WO | 2018138272 A1 | 8/2018 |
| WO | 2018138274 A1 | 8/2018 |

OTHER PUBLICATIONS

Brittain's publication, crystalline and pharmaceutical composition, 1999, pp. 348-361.*
Bernstein, "Polymorphism in Molecular Crystals", Oxford University Press, Oxford, 2002, pp. 9-10.
International Council for Harmonisation of Technical Requirements for Pharmaceuticals for Human Use, "Impurities: Guideline for Residual Solvents Q3C(R6)", 2016, ICH Expert Working Group.
Porter, "Coating of Pharmaceutical Dosage Forms", The Science and Practice of Pharmacy, 2006, pp. 929-938, Edition 21, Lippincott Williams & Wilkins, Philadelphia.
Rudnic et al., "Oral Solid Dosage Forms", The Science and Practice of Pharmacy, 2006, pp. 889-928, Edition 21, Lippincott Williams & Wilkins, Philadelphia.

* cited by examiner

*Primary Examiner* — Rei Tsang Shiao
(74) *Attorney, Agent, or Firm* — The Webb Law Firm

(57) ABSTRACT

The present invention provides a novel crystalline form of Eluxadoline, Eluxadoline Form APO-I, a co-crystal of Eluxadoline and methyl nicotinate, compositions and processes for the preparation thereof, and the use of this crystalline form in the treatment of opioid-modulated disorders, and in particular, gastrointestinal disorders, including irritable bowel syndrome with diarrhea (IBS-D).

7 Claims, 1 Drawing Sheet

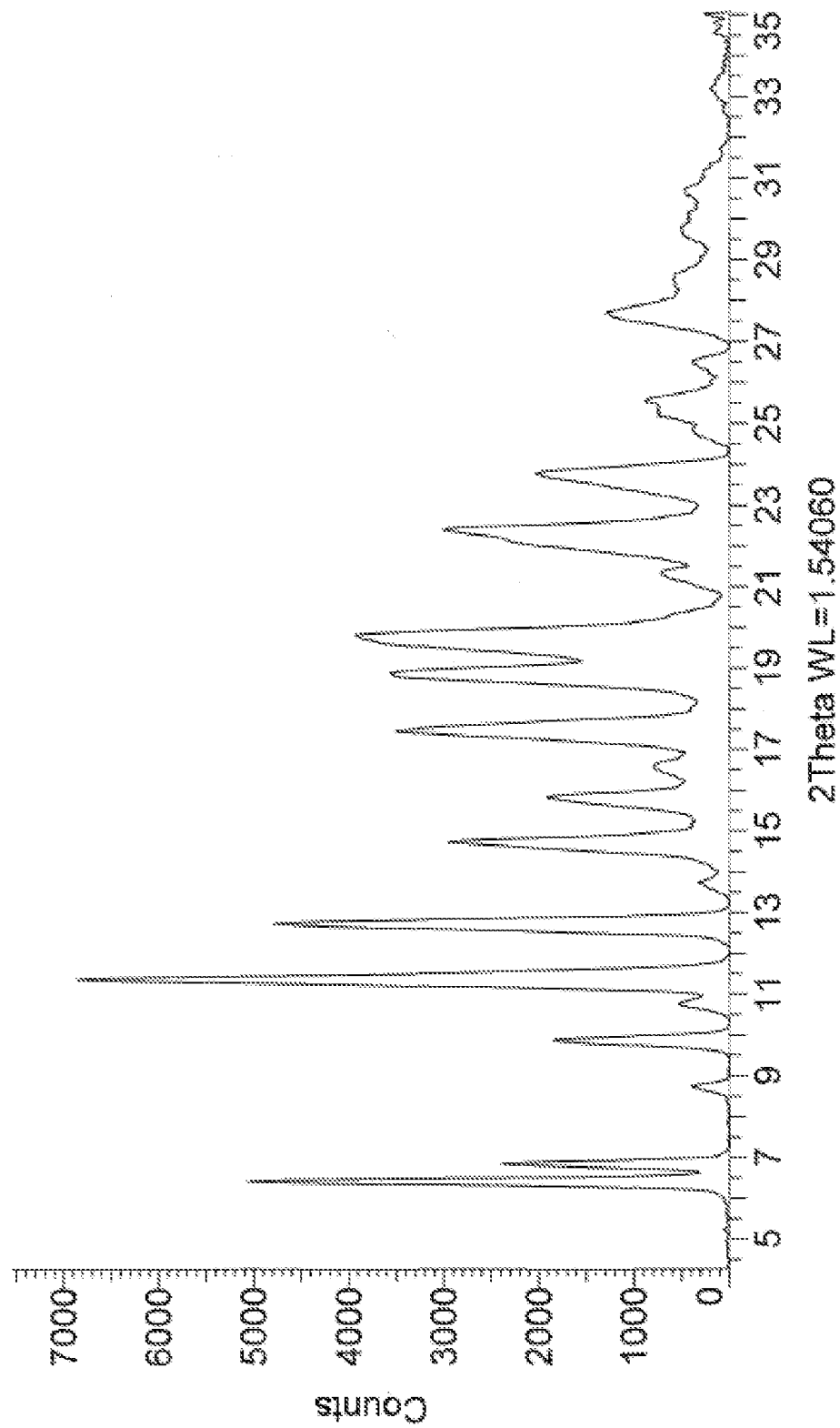

CRYSTALLINE FORM OF ELUXADOLINE

CROSS-REFERENCE TO RELATED APPLICATION

This application claims the benefit of U.S. Provisional Patent Application No. 62/562,654, filed Sep. 25, 2017, the disclosure of which is hereby incorporated in its entirety by reference.

TECHNICAL FIELD

The present invention is directed to a novel crystalline form of Eluxadoline, pharmaceutical compositions containing this form, processes for its preparation, and its use in the treatment of opioid-modulated disorders, including irritable bowel syndrome.

BACKGROUND

The compound 5-({[(2S)-2-amino-3-(4-carbamoyl-2,6-dimethylphenyl)propionyl]-[(1S)-1-(4-phenyl-1H-imidazol-2-yl)ethyl]amino}-methyl)-2-methoxybenzoic acid, commonly known as Eluxadoline, is described in WO 2003/092688 A2. Eluxadoline is an opioid receptor modulator, and is marketed in the United States as VIBERZI® for the treatment of irritable bowel syndrome with diarrhea (IBS-D).

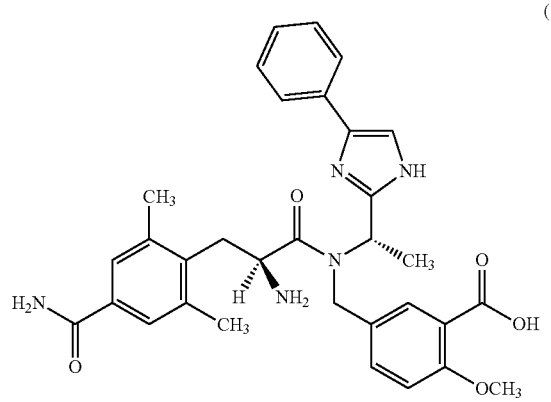

(1)

Crystalline forms of Eluxadoline, including hydrated and solvated forms, are reported, for example, in WO 2009/009480 A2, WO 2017/015606 A1 and WO 2017/114446 A1. However, these reported crystalline forms are associated with various problems, such as hygroscopicity, tendency to desolvation/dehydration during drying procedures or upon exposure to low humidity conditions; poor characterization leading to questions of controllability and reproducibility, the incorporation or use of solvents classified as toxic according to established ICH (International Council for Harmonisation of Technical Requirements for Pharmaceuticals for Human Use) guidelines such as Q3C(R6), or preparations that are impractical for commercial use. The tendency of forms to desolvate/dehydrate limits their usefulness in commercial products since it requires specialised practices to avoid desolvation/dehydration during drying, handling, storage and formulation activities. Furthermore, the variable and/or undefined nature of some of these forms has regulatory implications, as the characteristics of an active pharmaceutical ingredient must be well-defined and controlled.

Different crystalline forms of the same compound may have different packing, thermodynamic, spectroscopic, kinetic, surface and mechanical properties. For example, different crystalline forms may have different stability properties. A particular crystalline form may be more sensitive to heat, relative humidity (RH) and/or light. Alternatively or additionally, a particular crystalline form may provide more compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Additionally, the particular solubility characteristics of a given crystalline form in relation to undesired impurities can result in differences in the chemical purity of different crystalline forms upon isolation. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more resistant to flow, or may be more difficult to filter and/or wash.

Although general approaches to crystalline form screening of active pharmaceutical ingredients are known, it is well established that the prediction of how a given compound will crystallize is not possible. Furthermore, prediction of the properties of any unknown crystalline forms, and how they will differ from other crystalline forms of the same compound, remains even more elusive (Joel Bernstein, *Polymorphism in Molecular Crystals*, Oxford University Press, New York, 2002, page 9).

Therefore, there exists a need for novel crystalline forms of Eluxadoline for use in providing improved drug products containing Eluxadoline and their manufacture.

SUMMARY OF THE INVENTION

The Eluxadoline crystalline form of the present invention exhibits differences in properties when compared to the known crystalline forms of Eluxadoline. Properties that differ between the invention and known crystalline forms of Eluxadoline include the following: packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactibility, tableting, handling, flow, and blending.

Differences in the properties of the crystalline form of the present invention provide practical advantages that can be exploited to meet specific needs in the manufacture and formulation of Eluxadoline. For example, the crystalline form of the present invention resists polymorph conversion following storage at 40° C./75% R.H. (relative humidity) for at least 10 days. Additionally, the Eluxadoline crystalline form of the present invention does not incorporate volatile components, such as alcohol solvents. These properties are of benefit during the drying, handling and storage of both the drug substance and drug product, wherein exposure to ambient conditions is possible, and wherein crystalline forms that are subject to moisture uptake or solvent displacement can be susceptible to polymorphic conversion or degradation. Furthermore, the process for manufacturing of the Eluxadoline crystalline form of the present invention that has been developed uses solvents established by the ICH Q3C(R6) guideline as being of low toxic potential ("Class 3"), which is preferable for production of pharmaceutical agents when compared to solvents in Classes 1 (Solvents to Be Avoided) or 2 (Solvents to Be Limited).

In addition, methyl nicotinate is included in the U.S. Food & Drug Administration's (FDA's) Everything Added to Food in the United States (EAFUS) list, which contains ingredients added directly to food that the FDA has either approved as food additives, or has listed or affirmed as being GRAS (Generally Recognized as Safe). The GRAS list is an inventory of substances generally recognized by the FDA as having been adequately shown to be safe under the conditions of intended use.

Accordingly, in a first aspect of the present invention, there is provided a crystalline form of Eluxadoline that is a co-crystal of Eluxadoline and methyl nicotinate. Preferably, in the co-crystal of the first aspect, the molar ratio of Eluxadoline to methyl nicotinate in the co-crystal is between approximately 1:0.5 and 1:1.5. More preferably, the molar ratio of Eluxadoline to methyl nicotinate in the co-crystal is approximately 1:1.

In a second aspect of the present invention, there is provided a crystalline form of Eluxadoline, APO-I, that is a co-crystal of Eluxadoline and methyl nicotinate characterized by a powder X-ray diffraction (PXRD) diffractogram comprising peaks, expressed in degrees 2θ (±0.2°), at 6.4°, 6.9° and 11.4°. In a preferred embodiment of the second aspect, the PXRD diffractogram further comprises at least three peaks, expressed in degrees 2θ (±0.2°), selected from the group consisting of: 8.7°, 9.9°, 12.7°, 14.8°, 15.8°, 17.5°, 18.9°, 19.8° and 23.8°. In a further preferred embodiment of the second aspect, the PXRD diffractogram further comprises peaks, expressed in degrees 2θ (±0.2°), at 8.7°, 9.9°, 12.7°, 14.8°, 15.8°, 17.5°, 18.9°, 19.8° and 23.8°. Preferably, the crystalline form of the second aspect of the invention provides a PXRD diffractogram that is substantially the same in appearance as the representative PXRD diffractogram of Eluxadoline Form APO-I provided in FIG. 1. In this second aspect of the invention, the molar ratio of Eluxadoline to methyl nicotinate is preferably approximately 1:1.

In a third aspect of the present invention, there is provided a pharmaceutical composition comprising a crystalline form of Eluxadoline according to the first or second aspects of the invention, and one or more pharmaceutically acceptable excipients. Preferably, the pharmaceutical composition is in the form of a solid dosage form. Most preferably, the pharmaceutical composition is a tablet.

In a fourth aspect of the present invention, there is provided a use of a crystalline form of Eluxadoline according to the first or second aspects of the invention, or the pharmaceutical compositions of the third aspect of the invention, in the treatment of opioid-modulated disorders. In a preferred embodiment of the fourth aspect, the opioid-modulated disorder is pain or a gastrointestinal disorder. In a further preferred embodiment of the fourth aspect, the gastrointestinal disorder is selected from the group consisting of ulcerative colitis, Crohn's disease, irritable bowel syndrome with diarrhea (IBS-D) and alternating irritable bowel syndrome. Most preferably, the gastrointestinal disorder is irritable bowel syndrome with diarrhea (IBS-D).

In a fifth aspect of the present invention, there is provided a process for preparing a crystalline form of Eluxadoline according to the first or second aspects of the invention, comprising combining methyl nicotinate and Eluxadoline in a solvent, and maintaining the mixture at a suitable temperature. In a preferred embodiment of the fifth aspect, the solvent is a C1-C3 alcohol selected from the group consisting of methanol, ethanol, n-propanol and 2-propanol. Preferably, the C1-C3 alcohol is 2-propanol. In a further preferred embodiment of the fifth aspect, the suitable temperature is between approximately room temperature and approximately 80° C., more preferably the suitable temperature is approximately 60° C. In another preferred embodiment of the fifth aspect, the Eluxadoline and methyl nicotinate are combined in a molar ratio of Eluxadoline: methyl nicotinate of between approximately 1:25 and approximately 1:60. Most preferably, the Eluxadoline and methyl nicotinate are combined in a molar ratio of between approximately 1:35 and approximately 1:55.

Other aspects and features of the present invention will become apparent to those ordinarily skilled in the art upon review of the following description of specific embodiments of the invention in conjunction with the accompanying figures.

BRIEF DESCRIPTION OF THE DRAWING

Embodiments of the present invention are described, by way of example only, with reference to the attached FIGURE.

FIG. 1 is a representative PXRD diffractogram of Eluxadoline Form APO-I as prepared in Example 1.

DETAILED DESCRIPTION

The Eluxadoline crystalline form of the present invention exhibits differences in properties when compared to the known crystalline forms of Eluxadoline. Properties that differ between the invention and known crystalline forms of Eluxadoline include the following: packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactibility, tableting, handling, flow, and blending.

These differences in the properties of the crystalline form of the present invention provide practical advantages that can be exploited to meet specific needs in the manufacture and formulation of Eluxadoline. For example, the crystalline form of the present invention resists polymorph conversion following storage at 40° C./75% R.H. for at least 10 days. Additionally, the Eluxadoline crystalline form of the present does not incorporate volatile components, such as alcohol solvents. These properties are of benefit during the drying, handling and storage of both the drug substance and drug product, wherein exposure to ambient conditions is possible, and wherein crystalline forms that are subject to moisture uptake or solvent displacement can be susceptible to polymorphic conversion or degradation. Furthermore, the processes developed for the manufacture of the Eluxadoline crystalline form of the present invention use solvents established by ICH Q3C (R6) guideline as being of low toxic potential ("Class 3"), which is preferable for production of pharmaceutical agents in Classes 1 (Solvents to be Avoided) or 2 (Solvents to Be Limited).

In addition, methyl nicotinate is included in the U.S. FDA's EAFUS list, which contains ingredients added directly to food that the FDA has either approved as food additives, or has listed or affirmed as being GRAS.

Depending on the manner in which the crystalline form of the present invention is prepared, and the methodology and instrument used for PXRD analysis, the intensity of a given peak observed in a PXRD diffractogram of the crystalline form may vary when compared to the same peak in the representative PXRD diffractogram provided in FIG. 1. Thus, differences in relative peak intensities between peaks in a PXRD diffractogram for a given crystalline form may be observed when compared to the relative peak intensities of the peaks in the representative PXRD diffractogram of FIG. 1. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIG. 1, it is understood that individual peak positions may vary between ±0.2° 2θ from the values observed in the representative PXRD diffractograms provided in FIG. 1 for the crystalline forms of the invention, or listed in Table 1. Such variations are known and understood by a person of skill in the art, and any such variations do not depart from the invention disclosed herein.

Further, it is understood that, depending on the instrument used for X-ray analysis and its calibration, uniform offsets in the peak position of each peak in a PXRD diffractogram of greater that 0.2° 2θ may be observed when compared to the representative PXRD diffractograms provided in FIG. 1. Thus, PXRD diffractograms of the crystalline forms of the present invention may, in some circumstances, display the same relative peak positions as observed in the representative PXRD diffractograms provided in FIG. 1, with the exception that each peak is offset in the same direction, and by approximately the same amount, such that the overall PXRD diffractogram is substantially the same in appearance as the PXRD diffractogram of FIG. 1, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIG. 1 for the crystalline form of the invention.

As used herein, the term 'crystalline form' refers to a substance with a particular arrangement of molecular components in its crystal lattice, and which may be identified by physical characterization methods such as PXRD. As used herein, the term crystalline form is intended to refer to both single-component and multiple-component forms. Single component forms of Eluxadoline, such as those known in the art, consist solely of Eluxadoline, in the repeating unit of the crystalline lattice of Eluxadoline. Multiple component forms of Eluxadoline, such as the co-crystal of the present invention, include crystalline forms of Eluxadoline wherein one or more molecules are also incorporated into the crystal lattice with Eluxadoline.

As used herein, the term 'co-crystal' refers to a multiple-component crystalline form containing both Eluxadoline and a co-former, methyl nicotinate, that is solid under ambient conditions.

Multi-component crystalline forms comprising more than one type of molecule, such as co-crystals, may have some variability in the exact molar ratio of their components depending on a variety of factors. For example, a molar ratio of components within a multi-component crystalline form provides a person of skill in the art information as to the general relative quantities of the components of the crystalline form. In many cases, the molar ratio may vary by ±20% from a stated range. For example, with respect to the present invention, a molar ratio of 1:1 should be understood to include the ratios 1:0.8 and 1:1.2, as well as all of the individual ratios in between.

As used herein, the term "room temperature" refers to a temperature in the range of 20° C. to 25° C.

Unless defined otherwise herein, the term "approximately", when used in reference to molar ratios, allows for a variance of plus or minus 10%.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of Eluxadoline, Eluxadoline Form APO-I, which is a co-crystal of Eluxadoline and methyl nicotinate. Preferably, in Eluxadoline Form APO-I, the molar ratio of Eluxadoline to methyl nicotinate is approximately 1:1.

Eluxadoline Form APO-I can be characterized by a PXRD diffractogram comprising, among other peaks, characteristic peaks, expressed in degrees 2θ (±0.2°), at 6.4°, 6.9° and 11.4°. Preferably, the PXRD diffractogram further comprises at least three peaks, expressed in degrees 2θ (±0.2°), selected from the group consisting of 8.7°, 9.9°, 12.7°, 14.8°, 15.8°, 17.5°, 18.9°, 19.8° and 23.8°. More preferably, the PXRD diffractogram further comprises peaks, expressed in degrees 2θ (±0.2°), at 8.7°, 9.9°, 12.7°, 14.8°, 15.8°, 17.5°, 18.9°, 19.8° and 23.8°. PXRD studies of capped and uncapped samples of Eluxadoline Form APO-I have shown that this crystal form is stable following storage in stability chambers maintained at 27° C./60% RH and 40° C./75% RH for at least 10 days.

An illustrative PXRD diffractogram of Eluxadoline Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the Eluxadoline Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Eluxadoline Form APO-I from FIG. 1

| Angle (° 2θ) | Relative intensity (%) |
|---|---|
| 6.42 | 73.9 |
| 6.86 | 34.9 |
| 8.74 | 5.7 |
| 9.88 | 27.0 |
| 11.39 | 100 |
| 12.74 | 69.8 |
| 14.75 | 43.0 |
| 15.83 | 27.9 |
| 17.46 | 51.3 |
| 18.89 | 52.0 |

TABLE 1-continued

Relative peak intensities of Eluxadoline Form APO-I from FIG. 1

| Angle (° 2θ) | Relative intensity (%) |
|---|---|
| 19.82 | 57.5 |
| 23.78 | 29.6 |

As described in Examples 1 to 3, Eluxadoline Form APO-I can be prepared by combining methyl nicotinate and Eluxadoline in a solvent, preferably a C1-C3 alcohol selected from the group consisting of methanol, ethanol, n-propanol and 2-propanol, and most preferably 2-propanol; and maintaining the mixture at a suitable temperature, preferably between approximately room temperature and approximately 80° C., and more preferably at approximately 60° C., followed by a brief period of cooling, if necessary. Preferably, Eluxadoline and methyl nicotinate are combined in a molar ratio of Eluxadoline:methyl nicotinate of between approximately 1:25 and approximately 1:60, more preferably between approximately 1:35 and approximately 1:55. Filtration of the resulting suspension provides Eluxadoline Form APO-I having a PXRD diffractogram consistent with FIG. 1. Preferably, washing of the damp filter cake with pure solvent prior to drying is avoided. Instead, if desired, following filtration and drying, the isolated Eluxadoline Form APO-I may be combined with a hydrocarbon solvent, preferably cyclohexane, and allowed to stir for a time under ambient conditions to wash away any impurities, such as excess methyl nicotinate. Further filtration and drying provides purified Eluxadoline Form APO-I, free of excess methyl nicotinate.

In a further embodiment of the invention, there is provided a pharmaceutical composition of a co-crystal of Eluxadoline and methyl nicotinate with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a tablet. Preferably, the pharmaceutical composition provides a dose of Eluxadoline that is equivalent to the 75 mg or 100 mg of Eluxadoline found in VIBERZI® drug products.

Suitable pharmaceutically acceptable excipients are preferably inert with respect to the crystalline form of Eluxadoline of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrollidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Other suitable excipients and the preparation of solid oral dosage forms is well known to person of skill in the art, and is described generally, for example, in Remington The Science and Practice of Pharmacy 21$^{st}$ Edition (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in Remington The Science and Practice of Pharmacy 21$^{st}$ Edition (Lippincott Williams & Wilkins: Philadelphia; 2006; Chapter 46).

EXAMPLES

The following non-limiting examples are illustrative of some of the aspects and embodiments of the invention described herein.

The Eluxadoline used as a starting material in the following examples was consistent with Eluxadoline Form a, which is reported in WO 2009/009480 A2. However, other polymorphic forms are equally suitable as starting material, provided that they have some solubility in the solvent system used such that dissolution of the initial crystalline form and crystallization of the co-crystal of the present invention occurs over the course of the preparation.

PXRD Analysis:

PXRD diffractograms were recorded on a Bruker D8 Discover powder X-ray diffractometer (Bruker-AXS, Karlsruhe, Germany). The generator was a Micro-focus X-ray source (IMSTube: Cu tube with 1.54184 A) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Example 1: Preparation of Eluxadoline Form APO-I

Eluxadoline (400 mg) was treated with a prepared solution (67 mL) of methyl nicotinate (24 g) in isopropanol (72 mL), and the resulting suspension was stirred at 60° C. for 3 hours. The suspension was then removed from the heat source and allowed to cool for approximately 15 minutes. The resulting solid was collected by filtration and dried in vacuo at room temperature overnight to afford Eluxadoline Form APO-I (457 mg). $^1$H NMR analysis of the solid (d$_6$-DMSO) showed a molar ratio of Eluxadoline:methyl nicotinate of approximately 1:1, as well as a mixture of rotamers (indicated as minor and major in assignment that follows below). The PXRD diffractogram of a sample prepared by this method is shown in FIG. 1.

$^1$H-NMR (DMSO-d$_6$, 400 MHz) δ: 9.09 (1H, d, J=1.84 Hz), 8.82 (1H, d, J=4.72 Hz), 8.30 (1H, J=6.36 Hz), 7.95, (2H br s), 7.87-7.15 (11H, m), 6.96 (1H, J=8.48 Hz), 6.83-6.77 (1H, m), 5.72 minor, 5.23 major (1H, q, J=6.9 Hz), 4.64-4.38 (m, 3H), 4.00 (1H, d, J=15.4 Hz), 3.89 (s, 3H), 3.72 major, 3.69 minor (s, 3H), 3.11-2.67 (6H, m), 2.38 major, 2.05 minor (3H, s), 1.43 minor, 1.12 major (d, 3H, J=6.9 Hz) ppm.

Example 2: Preparation of Eluxadoline Form APO-I

Eluxadoline (500 mg) was treated with a prepared solution (15 mL) of methyl nicotinate (24 g) in isopropanol (72 mL), and the resulting suspension was stirred at 60° C. for 4 hours. The suspension was then removed from the heat source and allowed to cool for approximately 5 minutes. The resulting solid was collected by filtration and dried in vacuo at room temperature overnight to afford Eluxadoline Form APO-I (462 mg). The PXRD diffractogram of a sample prepared by this method was consistent with the PXRD shown in FIG. 1.

Example 3: Preparation of Eluxadoline Form APO-I

Eluxadoline (450 mg) was treated with a prepared solution (13.5 mL) of methyl nicotinate (5 g) in isopropanol (15 mL), and the resulting suspension was stirred at 60° C. for 3 hours. The suspension was then removed from the heat source and the solid immediately collected by filtration and dried in vacuo at room temperature overnight to afford crude material (455 mg). To remove any excess methyl nicotinate, the crude Eluxadoline Form APO-I was suspended in cyclohexane (2.5 mL), stirred for approximately 15 minutes, and the solid was again collected by filtration, with the residual methyl nicotinate being removed along with any other soluble impurities, to afford Eluxadoline Form APO-I (430 mg). The PXRD diffractogram of a sample prepared by this method was consistent with the PXRD shown in FIG. 1.

What is claimed is:

1. A crystalline form of Eluxadoline that is a co-crystal of Eluxadoline and methyl nicotinate characterized by a PXRD diffractogram comprising peaks, expressed in degrees 2θ (±0.2°), at 6.4°, 6.9° and 11.4.

2. The co-crystal of claim 1, wherein the molar ratio of Eluxadoline to methyl nicotinate is between approximately 1:0.5 and approximately 1:1.5.

3. The co-crystal of claim 1, wherein the molar ratio of Eluxadoline to methyl nicotinate is approximately 1:1.

4. The co-crystal of claim 1, further comprising at least three peaks, expressed in degrees 2θ (±0.2°), selected from the group consisting of: 8.7°, 9.9°, 12.7°, 14.8°, 15.8°, 17.5°, 18.9°, 19.8° and 23.8°.

5. The co-crystal of claim 1, further comprising peaks, expressed in degrees 2θ (±0.2°), at 8.7°, 9.9°, 12.7°, 14.8°, 15.8°, 17.5°, 18.9°, 19.8° and 23.8°.

6. The co-crystal of claim 1, providing a PXRD diffractogram substantially the same in appearance as the PXRD diffractogram provided in FIG. 1.

7. The co-crystal of claim 4, wherein the molar ratio of Eluxadoline to methyl nicotinate is approximately 1:1.

* * * * *